Figure 6:
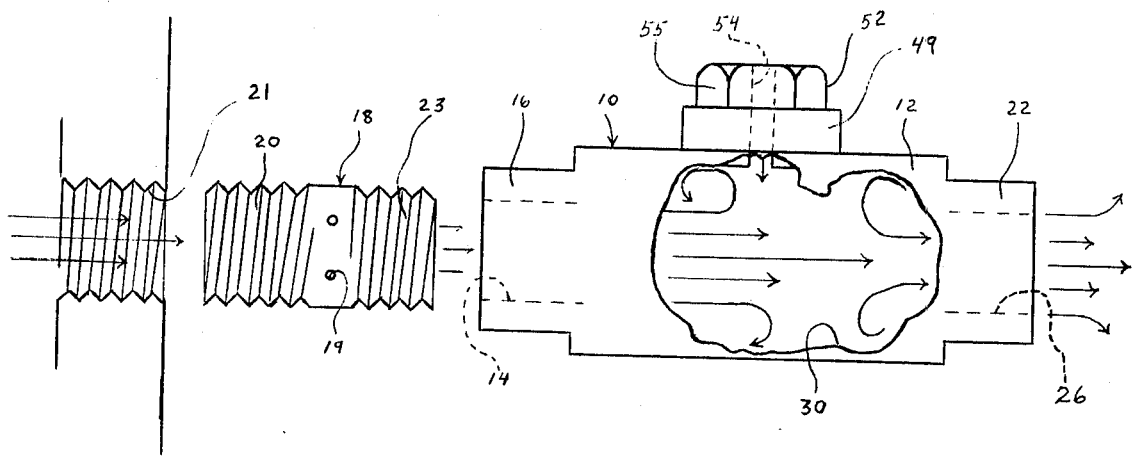

United States Patent [19]

Ivandick et al.

[11] 4,269,353

[45] May 26, 1981

[54] EXHAUST OPERATED VAPORIZER

[76] Inventors: Tony J. Ivandick, 2593 Shorewood Dr.; Mark J. Ivandick, 2287 Bensonhurst Dr., both of Florissant, Mo. 63031

[21] Appl. No.: 71,099

[22] Filed: Aug. 31, 1979

[51] Int. Cl.³ ............................................. A01M 19/00
[52] U.S. Cl. ................................................... 239/77
[58] Field of Search ..................... 239/77, 129; 43/125, 43/128, 129, 130, 132 A; 60/39.77; 252/359 CG

[56] References Cited

U.S. PATENT DOCUMENTS

| 2,901,182 | 8/1959 | Cragg et al. | 239/129 |
| 3,141,615 | 7/1964 | Waldron, Jr. | 239/129 X |

FOREIGN PATENT DOCUMENTS 180468  6/1922  United Kingdom .................... 239/129

Primary Examiner—Andres Kashnikow

[57] ABSTRACT

A device for vaporizing a liquid, powder, or solid and dispersing a vapor or fog including a body portion having a vaporizer chamber therein, the body portion having inlet and outlet end portions, each portion having a port therein, the ports having associated therewith a threaded passageway extending into the chamber, the body having a transverse opening therethrough intersecting the vaporizer chamber at an intermediate location along the top portion thereof, the opening having associated therewith a mating portion adapted to engage a valve to meter and supply a flow of liquid or to deliver a powder or solid into the vaporizer chamber, a variable length connecting member associated with the first end portion for attaching the device to the exhaust opening of an internal combustion engine, a vibratile channel shaped member positioned in the chamber, a tubular member having inlet and outlet portions with a discharge passageway therethrough, the tubular member having threads associated with the inlet portion thereof so as to be cooperatively engageable with the threaded passageway associated with the inlet port of the device and at its opposite end to register with and slidably engage the channel of the vibratile member, the tubular member also being of sufficient length to extend into the chamber to a point beyond the transverse opening, whereby the material to be vaporized is allowed to enter the exhaust heated chamber through the transverse opening therein, contacting the hot tubular and hot channel shaped members thus vaporizing the material, mixing the exhaust with the vapor so produced, and expelling the mixture from the outlet end portion of the device.

12 Claims, 8 Drawing Figures

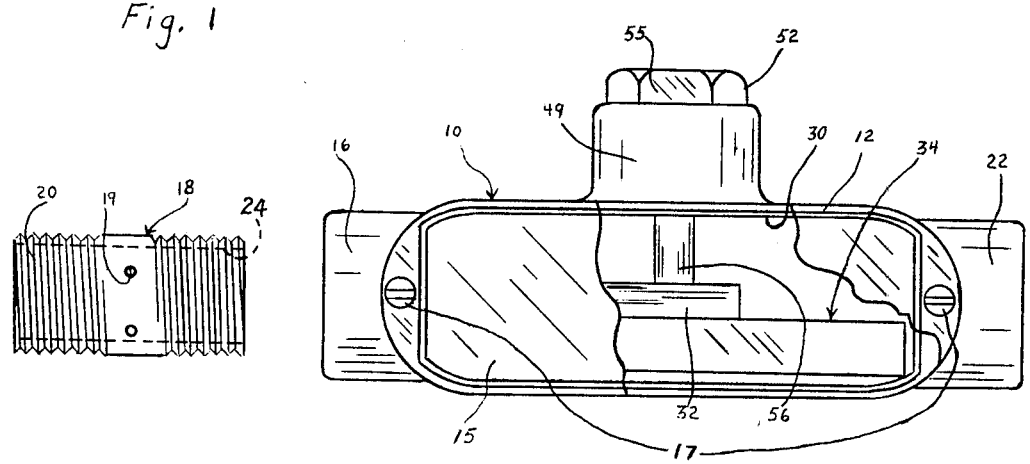
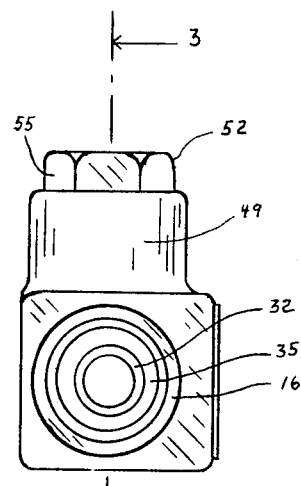
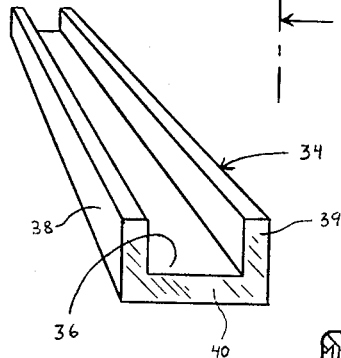
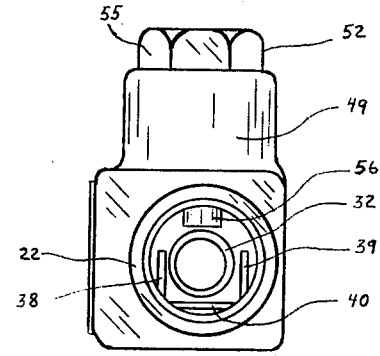
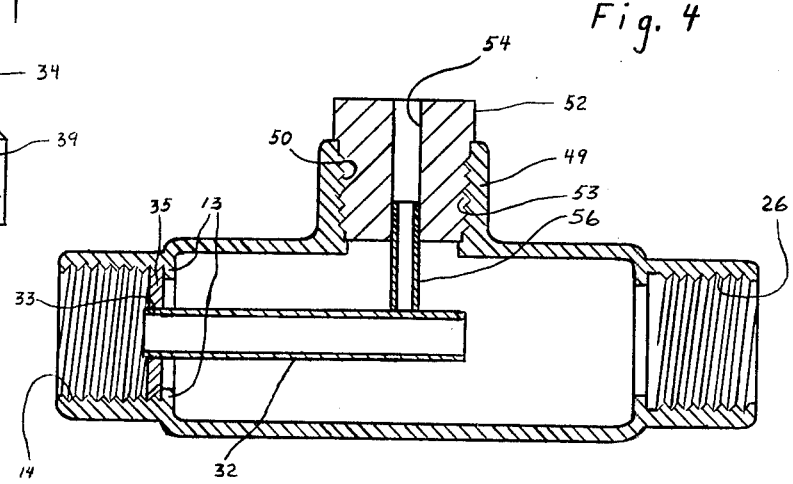

EXHAUST OPERATED VAPORIZER

Many different kinds of vaporizing or fogging devices are known and have been employed for use in vaporizing a liquid pesticide and distributing the vapor which contains particles of pesticide in the form of a fog. All such devices suffer from numerous disadvantages and shortcomings including being costly, extremely complex in both mechanical structure and operation, and difficult to maintain. The present device overcomes these disadvantages and shortcomings and is especially useful in a lawn and garden environment where it is necessary to control the pest population to promote health, comfort and economic well being. In addition to the aforementioned advantages, the device requires no formal instruction to operate and represents a low cost individual means to rid your living area of unwanted pests.

The known prior art devices include a variety of fogging and mist devices adapted for use with the exhaust from an internal combustion engine or device, see for example the constructions shown in W. Durr. et al U.S. Pat. No. 2,926,855 and C. W. Loy et. al U.S. Pat. No. 2,611,992. The known constructions for the most part are characterized by complicated self-contained units that require among other things to properly function, compressors, atomizing nozzles, valves, pressurized containers and acoustic jet resonators to be used in conjunction with an internal combustion device such as a pulse jet engine which produces the heat of vaporization and the high velocity gases which expel the fog or mist. Other more pertinent fogging devices adapted to be attached to the exhaust pipe of an internal combustion engine although much simpler than those of the type described above still require relatively complicated constructions, which employ axially alligned venturies, nozzles or jets, baffles, pressurized withdrawal of the insecticide from a storage tank, and valves in order to properly function. Although the fogging devices disclosed in the above identified patents have attempted to improve the capability of producing and expelling pest killing fogs at high velocities, many disadvantages and shortcomings still exist. One principal problem with the known devices is the inevitable clogging of spray nozzles, this is especially so when petroleum base pesticides are used with pressurized jets or atomizer nozzles. Prior art constructions require continual maintenance preferably after repeated use in order to prevent clogging, which is extremely difficult in the more complicated devices oftentimes requiring expensive and time consuming disassembly, maintenance, or replacement of defective nozzle parts. Thus prior art devices enjoy limited usefulness since they are constructed to vaporize only liquid materials which is evident by their use of atomizers and nozzles thereby structurally eliminating any use of a powder or solid with these devices. The known devices are also relatively large and difficult to operate thus being more adaptable for use by trained personnel more commonly employed by a municipality or commercial exterminator. This situation leaves the individual at a loss since he has relatively little control over the time and place of municipal fogging, nor can he afford to purchase and operate his own personal fogging device due primarily to the expense and operating costs of the known devices. Furthermore, no known device has been able to work efficiently using only the heat and velocity of exhaust gasses emitted from an internal combustion engine without requiring compressors, pressurized insecticide delivery systems or externally induced high velocity air flows to atomize and disperse the fog or mist. For these and other reasons, the known constructions have traditionally limited the scope of individual use.

The present construction overcomes these and other shortcomings and disadvantages of known fogging devices including the fogging devices constructed to utilize in some manner the exhaust of an internal combustion engine disclosed in the named patents, and teaches the construction and operation of a relatively simple device which is capable of vaporizing a liquid, powder, and solid, while at the same time remaining relatively inexpensive to make, use and repair. The present device is also easy to install on the exhaust system of most internal combustion engines and increases the versatility and flexibility of such devices.

The present vaporizing device includes a body portion having a vaporizer chamber therein, the body has an inlet end portion that has means for connecting to a tubular connecting member which in turn is connected to the exhaust outlet of an internal combustion engine. The opposite end of the chamber portion has an outlet end portion which has means for connecting to a hose thus permitting a pest killing fog to be directed into borrows or holes depending on the habitat of the pest to be exterminated. The inlet end portion has an inlet port with a closed passageway extending therethrough in communication with the vaporizer chamber. The closed passageway has means therealong for cooperatively engaging a tubular member of sufficient length so as to extend into the chamber. The tubular member has inlet and outlet end portions and a closed passageway therethrough, the tubular member communicates at its inlet end portion with the closed passageway through the inlet end portion of the body and at its outlet end portion with the interior of the chamber. The body portion of the vaporizer at an intermediate location therealong has an opening therethrough which intersects the chamber, the opening has a mating portion adapted to receive a member that has an orifice therethrough and means associated thereon for attaching suitable valve means and or a material storage container. The member associated with the opening can also be of a type which permits a solid or powder to be introduced into the chamber. Also of special importance to the present construction is the provision of a tubular member of sufficient length to extend into the chamber portion to a location beyond the transverse opening as well as a tubular guide member which is slidably positioned in the orifice associated with the opening member and has an end that rests on and abuts the tubular member therealong. The tubular guide member permits the flow of fluid or powder therethrough and directs it to the tubular member which is at a sufficiently high temperature that the liquid or solid that contacts it is substantially vaporized. Also important is the fact that the tubular member outlet portion vents inside the vaporizer chamber which permits the hot exhaust gasses that are flowing at a relatively high velocity to mix with the vapor and to further reduce the vapor particle size within the chamber before discharging the vapor through the outlet end portion of the device. A vibratile channel shaped member is movably positioned on the bottom portion of the chamber. The channel shaped member is shaped and dimensioned so that the tubular member extends through the channel and is engageable therewith. This construction enables any excess liquid or solid to collect in the channel shaped member and therein be repeatedly impinged against the tubular member producing substantial vaporization of the material to be vaporized. It is especially important to the present vaporizing device that the channel shaped member be movably positioned in the chamber so that the natural vibrations of the internal combustion engine will agitate the member thereby enhancing the efficiency of the device by permitting increased vaporization and reducing the build-up of any excess material to be vaporized. Although it is anticipated that the present device will primsrily be used with lawnmowers, it can also be used with any device that utilizes an internal combustion engine where hot exhaust gasses are expelled into the atmosphere. Typical other applications include use with electrical generators, lawn tractors, tillers, power grass edgers, and use in other similar internal combustion powered devices.

Figure 7:
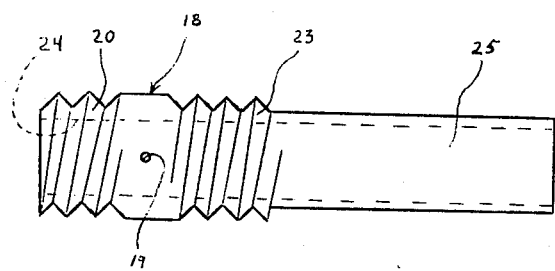
Figure 8:
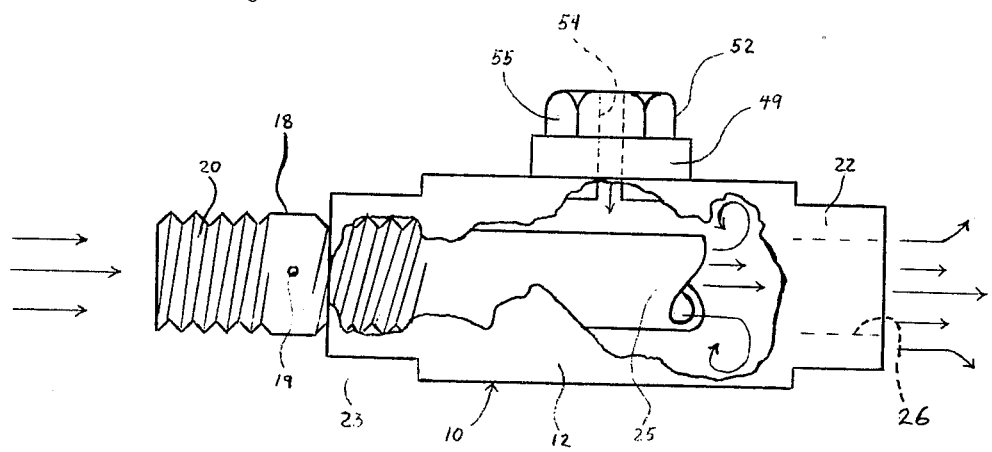

It is a principal object of the present invention to provide an attachment for an internal combustion engine capable of efficiently vaporizing a pesticide and dispensing a pest killing vapor by utilizing the hot exhaust gasses therefrom.

Another object is to provide a vaporizing device that is lightweight and compact in size that can easily be attached to lawn and garden equipment and be retained thereon when not in use.

Another object is to teach the construction and operation of a relatively simple, versatile and easy to operate vaporizing device which utilizes the normally wasted energy associated with exhaust gasses of an internal combustion engine.

Another object is to provide a vaporizing device that is relatively inexpensive to manufacture and use.

Another object is to provide a vaporizing device that conserves energy by functioning solely on the normally wasted energy associated with an internal combustion engine.

Another object is to provide a vaporizing device which can be independently controlled and operated while performing a task such as mowing the lawn or tilling a garden.

Another object is to provide a vaporizing device which requires relatively little maintenance.

Another object is to provide a vaporizing device which contains a mating portion associated with the outlet end portion for attaching a hose to direct the vapor into close areas such as pest borrows, hollow tree trunks, or crawl spaces under homes.

Another object is to provide a vaporizing device which can vaporize a liquid, powder, and solid.

These and other objects and advantages of the present invention will become apparent to those skilled in the art after considering the following detailed specification in conjunction with the accompanying drawings, wherein:

FIG. 1 is a side elevational view of the vaporizer device with a portion of a detachable cover plate removed showing the interior of the vaporizer chamber constructed according to the present invention;

FIG. 2 is an end elevational view of the inlet end portion;

FIG. 3 is an end elevational view of the outlet end portion;

FIG. 4 is a cross-sectional view taken along line 3—3 of FIG. 2;

FIG. 5 is a perspective view of the channel shaped member per se of FIGS. 1 and 3;

FIG. 6 is a side elevational view of the vaporizer device with a portion of the body removed exposing the vaporizer chambe and showing the exhaust opening of a conventional internal combustion engine with directional arrows provided to show the flow of gasses and material into and from the device;

FIG. 7 is a side elevational view of the tubular connecting member per se of FIG. 8; and FIG. 8 is a side elevational view of the vaporizer device exposing the interior thereof.

Referring to the drawings more particularly by reference numbers wherein like numerals refer to like parts, number 10 refers generally to an exhaust operated vaporizer constructed according to the present invention. The device 10 as shown in FIGS. 1 and 4 includes a body portion 12 having a annular projecting flange portion 13 formed at the mouth of threaded passageway 14 of inlet end portion 16 the importance of which will be hereinafter explained. The inlet end portion 16 threadedly receives a tubular fitting member 18. Tubular fitting member 18 has a passageway 24 extending therethrough and threaded portions 20 and 23 which cooperatively engage threaded passageway 14 and at its opposite end a threaded exhaust opening 21 of a conventional internal combustion engine see FIG. 6. Member 18 may also have one or a plurality of vent openings 19 formed therealong intersecting passageway 24 provided to prevent any substantial increase in back pressure experienced when the device is attached to the engine. Vent openings 19 are also important because instead of letting the exhaust gasses escape into the atmosphere it is contemplated that the gasses could be channeled back into the main flow of gasses thereby increasing the temperature of the chamber or increasing the outlet velocity of the expelled vapor. These channeled gasses may also be useful in assisting the gravity flow of a liquid pesticide from a closed container by relieving the vacuum commonly associated with liquid flow from a closed container or even to assist the gravity flow of a micro-pulverized powder into the device. FIGS. 7 and 8 show a tubular fitting member 18 with an extended outlet end portion 25 being long enough to extend into the vaporizer chamber, which is important to the present vaporizer construction for reasons hereinafter given. The outlet end portion 22 of the body 12 also has a threaded passageway 26 (FIG. 4) for receiving a threaded hose adapter (not shown) which cooperatively engages a hose used to direct the flow of vapor to a desired location or to a close hard to reach area. Even though the connection means are shown as tubular threaded fitting members which cooperate with threaded passageways 14 and 24 for ease in mating variable sized exhaust openings and hoses to the subject device other suitable connection means including hose clamps, bayonent-type connecting means or external threads formed on inlet and outlet end portions 16 and 22 could be used.

The body portion has an inner chamber 30 which extends between the opposite threaded end passageways 14 and 26. The body is also shown as having a removable cover plate 15 attached thereto by identical threaded members 17. Even though a closed body would function equally as well see FIGS. 6 and 8, the cover plate is preferably provided to increase the versatility of the device by permitting access into chamber 30 in order to provide an additional means to place solid materials to be vaporized into the device as well as to permit access into the chamber for maintenance or modification of the device. Chamber 30 receives an open ended tubular member 32 as clearly shown in FIGS. 1, 3 and 4. The member 32 has treads or other suitable connecting means formed adjacent to the inlet portion 33 thereof for cooperatively engaging an externally threaded washer-type member 35 which cooperatively engages threaded passageway 14 and preferably bears against the circular projecting flange 13 and is held in place thereagainst by the compressive force exerted by member 18 which bears against the opposite side of washer member 35 when the device is attached in the operative configuration. However it is also contemplated that tubular member 32 be formed integrally with vaporizer body 12 in the vicinity of threaded passageway 14 or projecting flange 13 thus eliminating the need for threaded attachment means and the washer-type member per se. The length of the tubular member is important to the present device for a variety of reasons. When substantial vaporization of the material entering the chamber is desired, the tubular member must be of a sufficient length to extend substantially through the chamber so that the material to be vaporized is first brought into contact therewith before allowing the fast moving exhaust gasses to vent inside the chamber thereafter permitting a vapor-exhaust mixture to be carried from chamber 30 through the outlet end passageway 26 into the atmosphere by the discharge velocity of the exhaust gasses. This construction reduces the amount of unvaporized material exiting the device by not subjecting the vaporizer material directly to the flow of fast moving exhaust gasses, but first allowing the material to come into contact with the hot chamber elements. Even though the tubular member is shown as having threaded connection means which cooperate with a washer member that in turn abuts flange 13 located at the mouth portion of threaded passageway 14, other suitable connecting means could be employed to attach tubular members of varying cross-sectional dimensions and lengths along the threaded passageway of inlet portion 16 including the use of an elongated connector member which can function as both connecting means to attach the device to a source of hot exhaust gasses as well as a tubular member, see FIGS. 7 and 8. When substantial heating of the material to be vaporized is not desired or when a micro-pulverized powder or dust is vaporized, the tubular member 32 can be shortened or eliminated altogether, see FIG. 6, so as to directly expose the material to the stream of fast moving exhaust gasses as they vent inside of chamber 30.

Chamber 30 has a vibratile channel shaped member 34 as shown in FIGS. 1, 3 and 5, which defines a channel 36 therein by opposite side walls 38 and 39 and a connecting wall 40 extnding therebetween. The channel shaped member 34 is shaped and dimensioned so that the tubular member 32 or elongated connecting member 18 can be slid onto and become substantially engageable with either of the walls 38 or 39 as shown in FIGS. 1 and 3 positioned on the member 32, such that member 32 extends substantially through channel 36. The connecting wall 40 of member 34 rests on the lower interior surface of chamber 30 and is allowed to vibrate thereon. The vibrating motion is caused by the natural vibrations set up in an operating internal combustion engine, as well as any additional movements of the machine the engine is powering. Even though the sidewalls 38 and 39 of member 34 are shown in a position to repeatedly contact member 32, it would also be possible to supply member 34 with means such as legs to raise it off of the lower interior surface of the chamber in order to bring connecting wall 40 into close proximity with member 32, thereby allowing all three walls of member 34 to engage the tubular member in a vibratile manner. The vibrating channel shaped member 34 is important to the present device and for reasons hereinafter given will readily become apparent to those skilled in the art. The upper portion of body 12 at an intermediate location therealong has a material inlet portion 49 which has a threaded opening or aperture 50 formed therethrough as shown in FIG. 4. The aperture 50 cooperatively receives a connecting member 52 having an orifice 54 extending radially therethrough. The connecting member includes a threaded portion 53 and a hexagonal portion 55 which cooperatively receives a wrench used for tightening it in place on the material inlet portion 49. Even though opening 50 is shown having member 52 with hexagonal portion 55 and orifice 54 so as to make it versatile enough to accept suitable valve or container means for respectively metering and supplying a desired volume of liquid or powder to the vaporizer chamber 30 other suitable adaptor means including those formed integrally with the body portion or material inlet portion of the device could also be used. The orifice 54 slidably receives a tubular guide 56. Guide 56 extends through aperture 50 of body 12 and engages tubular member 32 at a location therealong. Guide 56 is important to the present vaporizer construction especially when substantial vaporization is desirable since it permits the material to be vaporized to come in contact with member 32 without first being partially vaporized and mixed with the flow of hot exhaust gasses moving through chamber 30 thus reducing the possibility of expelling unvaporized material from the device. Tubular guide 56 is also important to the operation of the present device since it will vibrate axially in orifice 54 thereby agitating the material to be vaporized. This vibratile motion is especially desireable when the material to be vaporized is a powder, dust or solid, since these materials have a tendency to cake and resist gravity flow. The constant agitating motion of tubular guide 56 will work to break up the material to be vaporized and allow it to flow freely thus improving the efficiency of the vaporizing device. The excess or unvaporized material passing over the surface of member 32 will be substantially collected in the channel 36 of member 34. Member 34 is important to the efficient functioning of the device since it prevents the accumulation of excess material in chamber 30 by collecting it therein and through its vibrating movements repeatedly inpinging the material against member 32 thereby substantially vaporizing all of the material entering the chamber.

The device 10 has been shown and constructed primarily to vaporize either a liquid, powder, or solid and then mix the vapor with fast moving exhaust gasses to form a gas-vapor mixture which is then expelled from the device, however, it may be desirable to vaporize and disperse a powder or micro-pulverized dust without substantially heating it before it exits the device. Such a task could also be easily accomplished by device 10 with no modifications, or by simply removing altogether or substantially shortening the length of tubular member 32 so that when the micro-pulverized dust enters chamber 30 through operture 50, it is immediately mixed with the stream of fast moving exhaust gasses which carrys the dust particles along and expells them from the device before any substantial heating takes place.

The simplicity, compactness, versatility and controlability of the subject vaporizing device greatly increases its usefulness and effectiveness for use in back yard fogging operations including fogging hard to reach areas with the optional hose attachment. Furthermore its unique design and ease of operation are also important factors.

Thus there has been shown and described a novel versatile vaporizing device for use with an internal combustion engine and like devices, which vaporizing device fulfills all of the objects and advantages sought therefor. Many changes, modifications, variations, and other uses and applications of the present vaporizer construction will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. An exhaust operated vapor producing device comprising a body portion having a chamber therein, said body portion having inlet and outlet ports formed therethrough which communicate with said chamber, said inlet port having a tubular connecting member associated therewith for operatively attaching said device to exhaust producing means, said tubular connecting member having a passageway extending therethrough, said body portion having an opening therethrough intersecting said chamber at an intermediate location therealong, means associated with said opening for introducing the material to be vaporized into said chamber, said means having a passageway extending therethrough, a tubular guide positioned in said passageway extending through said means associated with said opening, said tubular guide extending into said chamber engaging said tubular connecting member at a location therealong, whereby the material to be vaporized is guided to said tubular connecting member and agitated by said tubular guide to insure a free flow of the material to be vaporized so that hot exhaust gases flow through said tubular connecting member into said chamber therein heating said chamber to a sufficient temperature so as to vaporize the material entering said chamber and mixing with the vapor so that a vapor-exhaust mixture is expelled through said outlet port.

2. An exhaust operated vapor producing device comprising a body portion including a chamber, said body portion having inlet and outlet end portions, each of said end portions having a port therein, each of said ports having a passageway extending into said chamber, said body portion having an opening therethrough intersecting said chamber at an intermediate location therealong, means associated with said opening having a passageway extending therethrough for introducing the material to be vaporized into said chamber, a tubular connecting member having a passageway extending therethrough for operatively attaching said vapor producing device to the exhaust opening of an internal combustion engine, an open ended tubular member positioned along said inlet passageway extending into said chamber, an open ended tubular guide positioned in said passageway extending through said means associated with said opening into said chamber abutting said tubular member at a location therealong, whereby the open ended tubular guide is allowed to vibrate axially in said passageway extending through said means associated with said opening to produce an agitating effect which breaks up the material to be vaporized producing a free flow thereof onto said open ended tubular member.

3. The device of claim 1 wherein said tubular connecting member has an outlet portion of sufficient length to extend into said chamber.

4. The device of claim 1 including means associated with said outlet port for attaching a hose-type member.

5. The device of claim 2 wherein said outlet end portion has connecting means associated therewith for attaching said device to a hose member.

6. The device of claim 1 or 2 wherein said tubular connecting member has means connecting one end thereof to said body portion, and means connecting the opposite end thereof to a source of hot exhaust gases.

7. The device of claim 1 or 2 wherein said tubular connecting member has an opening or openings therethrough intersecting its passageway at a location therealong.

8. The device of claim 1 or 2 wherein said means associated with said opening for introducing the material to be vaporized includes a connecting member having means connecting one end of said connecting member to said body portion, and means connecting the opposite end thereof to a material storage container.

9. An exhaust operated vapor producing device comprising a body portion having a chamber therein, said body portion having inlet and outlet ports formed therethrough which communicate with said chamber, said inlet port having a tubular connecting member associated therewith for operatively attaching said device to exhaust producing means, said tubular connecting member having a passageway extending therethrough, a channel shaped member positioned in said chamber, said body portion having an opening therethrough intersecting said chamber at an intermediate location therealong, means associated with said opening for introducing the material to be vaporized into said chamber, said means having a passageway extending therethrough, whereby operation of said source of hot exhaust gases vibrates said channel shaped member thereby causing repeated contact with said tubular connecting member as hot exhaust gases flow through said tubular connecting member into said chamber therein heating said chamber and channel shaped member to a sufficient temperature so as to vaporize the material entering said chamber and mixing with the vapor so that a vapor-exhaust mixture is expelled through said outlet port.

10. An exhaust operated vapor producing device comprising a body portion including a chamber, said body portion having inlet and outlet end portions, each of said end portions having a port therein, each of said ports having a passageway extending into said chamber, said body portion having an opening therethrough intersecting said chamber at an intermediate location therealong, means associated with said opening having a passageway extending therethrough for introducing the material to be vaporized into said chamber, a tubular connecting member having a passageway extending therethrough for operatively attaching said vapor producing device to the exhaust opening of an internal combustion engine, an open ended tubular member positioned along said inlet passageway extending into said chamber, a channel shaped member positioned in said chamber to slideably engage said tubular member extending into said chamber, an open ended tubular guide positioned in said passageway extending through said means associated with said opening into said chamber abutting said tubular member at a location therealong, whereby hot exhaust gases flow into said chamber, mix with the vapor formed therein, and are discharged through said outlet end portion.

11. The device of claim 9 including a tubular guide positioned in said passageway extending through said means associated with said opening, said tubular guide extending into said chamber engaging said tubular connecting member at a location therealong, whereby the material to be vaporized is agitated and guided to said tubular connecting member.

12. The device of claim 9 or 10 wherein said tubular connecting member has an opening or openings therethrough intersecting said passageway at a location therealong.

* * * * *